US00PP33310P2

(12) United States Plant Patent
Hansen

(10) Patent No.: US PP33,310 P2
(45) Date of Patent: Aug. 3, 2021

(54) ***PEROVSKIA* PLANT NAMED 'SAGE ADVICE'**

(50) Latin Name: ***Perovskia atriplicifolia* (Benth.)**
Varietal Denomination: Sage Advice

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,230

(22) Filed: Nov. 19, 2020

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./263.1, 226
CPC ... A01H 5/02; A01H 5/12; A01H 5/00; A01H 6/50
See application file for complete search history.

(56) References Cited

U.S. PATENT DOCUMENTS

PP27,526 P2 * 1/2017 Hurd ..... A01H 5/02
Plt./263.1

OTHER PUBLICATIONS

Digger Magazine Farwest New Varieties Showcase 2020, retrieved on Mar. 16, 2021, retrieved from the Internet at http://www.diggermagazine.com/wp-content/uploads/2020/08/New-Varieties-2020-Final.pdf, pp. 34-48. (Year: 2020).*

* cited by examiner

*Primary Examiner* — June Hwu

(57) ABSTRACT

The new and distinct cultivar of ornamental, hardy, Russian Sage plant, *Perovskia* 'Sage Advice' with short, dense habit of strong erect stems that remain upright through the growing season. The new plant is vigorous with many large, densely-arranged, rich lavender-purple flowers on branched stems. Foliage is silvery-green, dissected, fragrant and is retained well throughout the growing season.

1 Drawing Sheet

Botanical classification: *Perovskia atriplicifolia* (Benth.).
Variety denomination: 'Sage Advice'.

STATEMENT REGARDING PRIOR DISCLOSURES UNDER 37 CFR 1.77(B)(6)

The first non-enabling disclosure of the claimed plant, in the form of a photograph and brief description on a website operated by Walters Gardens, Inc. on Feb. 2, 2020. Subsequently, the new plant was advertised in the "Walters Gardens 20-21 Catalog" by Walters Gardens, Inc. released on May 20, 2020. The claimed plant was first sold privately to Four Star Greenhouse, Inc. on Mar. 2, 2020 by Walters Gardens, Inc., who obtained the plant and all information relating thereto, from the inventor. No plants of *Peroskia* 'Sage Advice' have been sold to the public in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct plant of Russian sage, botanically known as *Perovskia* 'Sage Advice' and will be referred to hereinafter also by its cultivar name 'Sage Advice' and the new plant. The new plant cultivar of *Perovskia* is a hardy herbaceous perennial grown for landscape use.

Seed was collected by the inventor on Nov. 3, 2014 at a wholesale perennial nursery in Zeeland, Mich. from an insect pollination between the proprietary, unreleased and unnamed seedling known only by the breeder code 13-1-1 as the female or seed parent with 'Rocketman' as the presumed to be male or pollen parent. The seed and sown in the winter of 2014 and the single seedling which produced *Perovskia* 'Sage Advice' was originally selected in the summer of 2016 and assigned the breeder code 14-1-3 through the remaining selection process. All subsequent evaluations were performed in a full-sun trial garden at the same nursery with loamy sand soil and irrigation and fertilizer as required. The plant was propagated by stem cuttings at the same nursery in Zeeland, Mich. and the original plant and the cuttings evaluated over the next two years until final approval for introduction in the summer of 2018. The resultant asexually propagated cuttings have been stable and identical to the original plant in successive asexual propagations.

SUMMARY OF THE INVENTION

*Perovskia* 'Sage Advice' differs from its parent as well as all other hardy Russian sage known to the inventor in a combination of traits. The following characteristics in combination distinguish 'Sage Advice' from all other *Perovskia* plants known to the inventor:

1. Short dense habit with strong, erect, dense stems that remain upright through the growing season;
2. Long flowering season of large, densely-arranged, rich lavender-purple flowers on branched stems;

3. Effective flowering time extended with dark smoky purple calyxes;
4. The foliage is silvery-green, cleft and fragrant.
5. Vigorous growth rate.

The nearest comparison plants known to the inventor are the parent plant *Perovskia* 'LISSLITT' U.S. Plant Pat. No. 20,845, 'Denim 'n Lace' U.S. Plant Pat. No. 28,445, 'Rocketman' U.S. Plant Pat. No. 27,526 and 'Blue Jean Baby' U.S. Plant Pat. No. 29,281. 'LISSLITT' is slightly shorter with less upright stems that are more prone to lodging, the habit is more open and the flowers are not as deep lavender-purple. 'Denim 'n Lace' has slightly smaller habit in height and width, the foliage is more finely doubly cleft and the flowers are not as deep lavender-purple. 'Rocketman' has foliage that is less dissected, the habit is slightly shorter, broader and more open. 'Blue Jean Baby' has flowers that are more lavender-blue and less lavender-purple, the flowering season begins slightly earlier, and foliage is more doubly cleft. The new plant calyces that are darker than all of the above cultivars.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plant used in the photograph is a three-year old plant grown in full sun field in loamy sand soil in trial gardens of a nursery in Zeeland, Mich.

DETAILED BOTANICAL DESCRIPTION

Figure 1:
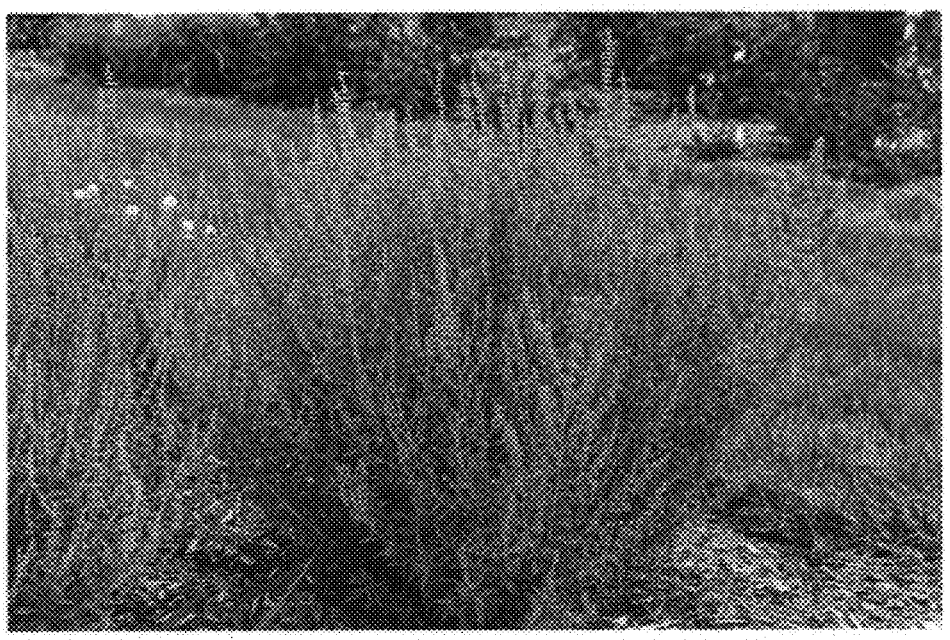
FIG. 1 shows 'Sage Advice' in the landscape.
Figure 2:
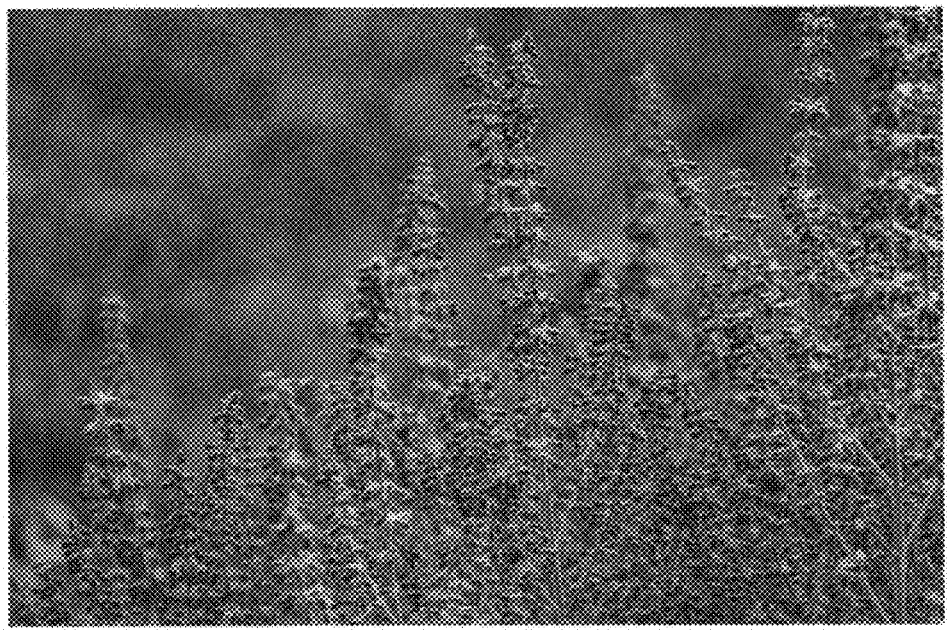
FIG. 2 shows a close-up of the flower stems of 'Sage Advice'.

The following is a detailed description of *Perovskia* 'Sage Advice' as observed and compared to other cultivars for five years in trial gardens and production fields at a nursery in Zeeland, Mich. The following description is of an six-year old plant of *Perovskia* 'Sage Advice' in a full-sun trial garden in Zeeland, Mich. with limited irrigation as needed and without any pinching or plant growth regulators. The new plant has not been observed under all possible environments, and the phenotype may vary slightly with different environmental conditions, such as temperature, light, fertility, moisture and maturity levels, but without any change in the genotype. The color descriptions are in accordance with the 2001 edition of The R.H.S. Colour Chart of The Royal Horticultural Society, London, England, except where common dictionary color terms are used.

Plant habit: Upright and dense mound; heavily oppositely branched; deciduous, semi-woody sub-shrub usually dying to the ground in most Michigan winters and re-sprouting with new stems from the base each spring; about 32 stems per plant;

Plant size: To about 92.0 cm in height, average stem height of about 88.0 cm, and about 90.0 cm in width at the widest point about 20 cm above soil;

Root description: Fibrous; color nearest RHS 155D;

Propagation: Stem cuttings; root initiation occurs in about 14 days at a temperature of 20° C.;

Growth rate: Vigorous;

Crop time: About 10 to 14 weeks to produce flowering plant from rooted plug;

Stem description: Quadangular; oppositely branched; young portions lanulose; older stems becoming woody at base; average about 88.0 cm long and about 6.0 mm across near base; about 18 branches per stem; with herbal fragrance;

Stem color: Between RHS 191B and RHS 191C;

Internode length: Average 3.5 cm;

Internode color: Same as surrounding stem;

Branches: Quadangular; opposite; lanulose; about 45° angle above horizontal in distal branches and about 30° angle above horizontal in proximal branches; lower branches about 17.0 cm long and about 1.2 mm diameter at base, decreasing distally to upper branches about 5.0 cm long and about 1.0 mm diameter;

Branch color: Nearest RHS 191D;

Foliage description: Opposite, broadly ovate; dissected nearly to about half way to midrib; acute apex and lobes, narrowly attenuate base; margin lobed to crenate, farinose on abaxial and puberulent on adaxial surface; to about 3.5 cm long and about 1.6 cm wide, shorter in distal region, average about 3.0 cm long and about 1.5 cm wide; with herbal fragrance;

Leaf color: Adaxial blend between RHS N138B and RHS 191B; abaxial blend between RHS N138C and RHS 191B;

Leaf venation: Pinnate; glandular adaxial and abaxial;

Vein color: Main adaxial vein nearest RHS 147B; abaxial midrib between RHS 145D and RHS 145C;

Petiole: Flattened ventral to dorsal or abaxial to adaxial; sessile to about 6.0 mm long and about 1.5 mm across, average about 4.5 mm long and about 1.2 mm across at stem;

Petiole color: Adaxial nearest RHS 147B; abaxial between RHS 145C and RHS 145D;

Peduncle: Main stems vertical, branched verticillate panicle; about 9.0 cm tall above last branch and about 2.0 cm across above last branch;

Peduncle color: Between RHS 148D and RHS 196A;

Pedicel: Terete; puberulent; curved slightly downward; about 1.0 mm long and 0.3 mm diameter;

Pedicel color: Nearest RHS 79A;

Flower buds about one day prior to opening: Terete; about 6.0 mm long and about 2.0 mm diameter; long ovoid; rounded apex; rounded base; abaxial calyx with dense pubescence about 1.0 mm long;

Bud color: Abaxial calyx hairs nearest RHS N82A; calyx base nearest RHS 145B, distally nearest RHS N92C; extended unopened petal nearest RHS N88A;

Flowers: Perfect, zygomorphic, bilabiate with upper and lower lip fused in about basal 6.5 mm; about 14.0 mm long to exserted style and about 6.0 mm across; face opening to nearly flat;

Inflorescence: Flowering in distal 32.0 cm and 14.0 cm wide; side branches with up to 14 verticils, up to 26 flowers per verticil, up to 220 flowers per branch, main center stem with up to 90 flowers per verticil and 700 flowers total up to 2400 flowers per total inflorescence stem;

Flower attitude: Outwardly to slightly drooping;

Fragrance: Slight herbal;

Corolla: Bilabiate; 11.0 mm long and 6.0 mm wide fused in basal 6.5 mm;

*Upper lip*.—Tri-lobed, puberulent adaxial; glabrous abaxial; center lobe obtuse to ovate, 3.0 mm long and 2.0 mm wide at fusion, rounded apex, entire margin;

side lobes rounded with rounded apex, 3.0 mm long and 2.5 mm wide, angled about 45° above horizontal.

*Lower lip*.—Single lobe, nearly flat with rounded apex and entire margin; about 6.5 mm long and about 1.0 mm wide at fusion point; basal 6.5 mm fused into tube; tube about 2.5 mm in width; glabrous abaxial, adaxial throat puberulent.

Corolla color: Upper lip distal adaxial and abaxial nearest RHS N88B with adaxial midrib nearest RHS N88A, proximal 4.0 mm adaxial and abaxial nearest RHS NN155D; lower lip adaxial and abaxial distally nearest RHS N88B without darker midrib, proximal 4.0 mm adaxial and abaxial nearest RHS 155D; adaxial corolla tube between RHS 91D and RHS NN155D, abaxial corolla tube between RHS 91D and RHS NN155D;

Gynoecium: One pistil; about 14 mm long;

*Style*.—About 12.5 mm long and about 0.3 mm diameter; proximal color white nearest RHS NN155D, distal 9.0 mm nearest RHS 76B.

*Stigma*.—Bifid in the terminal 0.5 mm, about 0.5 mm across; color white nearest RHS NN155D with a light blush nearest RHS N82D.

*Ovary*.—Oblong globose; about 1.0 mm long and 0.7 mm across; color between RHS 150D and RHS 145D.

Androecium: four, in two sets, two longer and distal fertile and two proximal and sterile;

*Filaments*.—Proximal fertile set cylindrical, adnate to corolla about 4.0 mm from base, curved upward about 2.5 mm long and 0.3 mm diameter; color white, nearest RHS NN155D; distal sterile set cylindrical, adnate to inner corolla about 6.0 mm from base, about 1.0 mm long and 0.2 mm diameter, color nearest RHS NN155D.

*Anther*.—Fertile pair elliptic; versatile; longitudinal; about 1.0 mm long and 0.5 mm across, color nearest RHS N187C; sterile pair globose, vestigial, about 0.2 mm diameter; color nearest RHS NN155D.

*Pollen*.—Abundant on fertile anthers; color nearest RHS 156D.

Calyx: Tubular campanulate; about 6.0 mm long and about 2.0 mm across (without hairs);

Sepals: Five; 6.0 mm long with upper three lobes split in distal 0.3 mm and lower two lobes split in distal 1.0 mm; apices acute; fused in basal 5.0 mm; margin entire; abaxial densely pubescent and glandular with hairs about 1.0 mm long, adaxial glabrous; persistent for weeks after flower abscission and drop;

Sepal color: Adaxial between RHS 146D and RHS 145A; abaxial nearest RHS 79A with portions not exposed to light nearest RHS 146D blushed with RHS 79A; abaxial hairs nearest RHS N82A;

Seed: Spatulate in outline, rounded apex and attenuate base; up to four per flower, typically one per flower; about 2.0 mm long and about 1.0 mm diameter at widest portion and about 0.5 mm thick; color nearest RHS 200A;

Hardiness of the new plant is at least U.S.D.A. zones 4 to 9. The new plant is highly resistant to drought once established.

Pest and disease resistance: Russian sage is typically resistant to deer and rodent browsing. The new plant is less prone to yellowing foliage and lower leaf drop than other known Russian sage cultivars. No other susceptibility or resistance to diseases or pests has been observed except that which is common to *Perovskia*.

It is claimed:

1. A new and distinct cultivar of hardy Russian sage plant, *Perovskia* 'Sage Advice' as herein described and illustrated.

* * * * *